United States Patent
Di Schiena

(10) Patent No.: US 9,050,351 B2
(45) Date of Patent: Jun. 9, 2015

(54) TOPICAL COMPOSITIONS DESIGNED TO MAINTAIN OR RESTORE THE INTEGRITY OF THE MUCOUS MEMBRANES

(75) Inventor: Michele Giuseppe Di Schiena, Robecco sul Naviglio (IT)

(73) Assignee: RICEFARMA S.R.L., Milan (IT)

( * ) Notice: Subject to any disclaimer, the term of this patent is extended or adjusted under 35 U.S.C. 154(b) by 348 days.

(21) Appl. No.: 13/046,094

(22) Filed: Mar. 11, 2011

(65) Prior Publication Data
US 2012/0135087 A1    May 31, 2012

(30) Foreign Application Priority Data
Nov. 30, 2010 (IT) .................... MI10A2218

(51) Int. Cl.
| | | |
|---|---|---|
| *A61K 33/38* | (2006.01) | |
| *A61P 29/00* | (2006.01) | |
| *A61K 36/886* | (2006.01) | |
| *A61K 31/683* | (2006.01) | |
| *A61K 36/484* | (2006.01) | |
| *A61K 31/685* | (2006.01) | |
| *A61K 9/00* | (2006.01) | |
| *A61K 31/728* | (2006.01) | |

(52) U.S. Cl.
CPC ............ *A61K 31/685* (2013.01); *A61K 9/0031* (2013.01); *A61K 9/0034* (2013.01); *A61K 9/0036* (2013.01); *A61K 9/0043* (2013.01); *A61K 9/0046* (2013.01); *A61K 9/0048* (2013.01); *A61K 9/006* (2013.01); *A61K 31/728* (2013.01)

(58) Field of Classification Search
USPC .......................... 424/618, 725, 744; 514/77
See application file for complete search history.

(56) References Cited

U.S. PATENT DOCUMENTS

| | | | |
|---|---|---|---|
| 2002/0049422 A1* | 4/2002 | Brewitt .................. | 604/500 |
| 2005/0143343 A1* | 6/2005 | Nerenberg .............. | 514/58 |
| 2006/0014813 A1* | 1/2006 | Connelly et al. ........ | 514/378 |

* cited by examiner

*Primary Examiner* — Mina Haghighatian
*Assistant Examiner* — Luke Karpinski
(74) *Attorney, Agent, or Firm* — Silvia Salvadori, P.C.

(57) ABSTRACT

The present invention relates to topical compositions containing choline alfoscerate for use in maintaining and restoring the integrity of the mucous membranes.

6 Claims, No Drawings

TOPICAL COMPOSITIONS DESIGNED TO MAINTAIN OR RESTORE THE INTEGRITY OF THE MUCOUS MEMBRANES

This application claims priority to and the benefit of Italian Application MI2010A002218 filed on Nov. 30, 2010, the content of which is incorporated herein by reference in its entirety.

FIELD OF INVENTION

The present invention relates to topical compositions containing choline alfoscerate which are useful to maintain and restore the integrity of the mucous membranes.

STATE OF THE ART

Choline alfoscerate is known as a nootropic substance, namely a substance which improves the trophism of the brain cells (by activating the blood supply and cell metabolism), and consequently the intellectual functions.

As disclosed in WO93/19730, choline alfoscerate is practically devoid of systemic toxicity, and has marked topical tolerability and a low incidence of skin irritation, eye irritation and skin sensitisation.

It is known in the pharmaceutical field for its use in injectable compositions and oral compositions for the treatment of alterations of the cognitive functions, and as a possible growth hormone secreting factor.

Its use in diet supplements for the same purposes as described for the pharmaceutical industry is also known.

In the dermatological and cosmetic field, for example in WO93/19730, its use on the skin and hair with a moisturizing, emollient, elasticizing, restorative, volume-enhancing action is disclosed.

The integrity of the mucous membranes can be affected by a variety of exogenous and endogenous causes, such as vitamin deficiencies, incorrect diet, poor hygiene, bacterial, viral or fungal infections, intestinal dysbiosis, alterations of the mucosal microbial flora, endocrine imbalances, debilitating diseases, hereditary factors, mechanical, physical, chemical and traumatic factors, radiation, etc.

There is still a need for new compositions useful to maintain and restore the integrity of the mucous membranes.

DESCRIPTION OF THE INVENTION

It has surprisingly been found that topical use of choline alfoscerate on the mucous membranes aids their cell trophism, thus maintaining and restoring the integrity of the mucosal tissue.

The term "trophism" means the general state of nutrition of an organism or part thereof.

The present invention therefore relates to topical compositions containing choline alfoscerate for use in the maintenance and restoration of the integrity of the mucous membranes.

The mucous membranes in question are preferably those commonly called external mucosae, such as the mucosa of the mouth and oral cavity in general, the nasal mucosa, ocular mucosa, auricular mucosa, the mucosa of the male and female genitals, and the anal and rectal mucosa.

According to a preferred aspect of the invention, topical compositions containing choline alfoscerate are useful, for example, in the prevention and treatment of inflammatory disorders and/or lesions of the oral mucosa, and in the prevention and/or treatment of damaged and/or inflamed gums.

Inflammation and lesions of the oral mucosa mean, for example, gingivitis, mucositis (mouth ulcers, including recurrent mouth ulcers), stomatitis, glossitis, etc. These disorders can have different etiologies; for example, they can have mechanical, chemical or pathological causes (infections, dysbiosis of the oral cavity or intestinal dysbiosis).

It has also been found that topical use of choline alfoscerate is useful to maintain the correct pH value of the oral mucosa.

According to a further aspect of the invention, the compositions are suitable for either human or veterinary use.

Choline alfoscerate is the internal salt of L-alpha-glycerylphosphorylcholine; it is an ampholyte, is highly soluble in water and ethanol, possesses high chemical and microbiological stability, and has special organoleptic properties in that it is practically flavorless, odorless and colorless.

These organoleptic properties facilitate its use in the topical compositions to which this invention relates, which are useful for the treatment of the mucosa of the mouth and oral cavity and the nasal mucosa in particular.

Choline alfoscerate is commercially available in both anhydrous and hydrated form; as the compound is markedly hygroscopic, the preferred form is the hydrated form.

Commercially available pharmaceutical-grade choline alfoscerate hydrate, with the following chemico-physical characteristics, can preferably be used to prepare the compositions:

Appearance: a clear, highly viscous fluid
Titer: 98.0-102.0% (on an anhydrous base)
Water (K.F.): 13.5%-16.5%
Specific rotation: between 2.40° and 2.95° (on an anhydrous base)
Solubility (in water 10% w/v): complete
pH: 5.0-7.0.

The concentration of choline alfoscerate in the topical compositions according to the present invention can be selected on the basis of the type of mucous membranes to be treated and the type of composition; for example, it can be between 0.001% w/v and 99% w/v.

The concentration of choline alfoscerate is preferably between 0.010% w/v and 50% w/v.

According to a further aspect, the topical compositions of the present invention can also include further active ingredients known for the topical treatment of the mucous membranes, such as those described in Martindale, The Complete Drug Reference, 34th Edition.

The further active ingredients are preferably mesalazine, i.e., mesalamine or 5-aminosalicylic acid (5-ASA), liquorice and derivatives thereof, silver and derivatives thereof, aloe vera, allantoin and derivatives thereof, chlorhexidine and benzalkonium chloride.

Topical compositions in the form of an anorectal or rectal enema containing choline alfoscerate and mesalazine can, for example, be advantageously used for the prevention and treatment of ulcerating colitis and Crohn's disease.

The compositions according to the invention can be formulated in a way suitable for topical administration, and can be prepared according to conventional methods well known to the prior art, such as those described in Remington, The Science and Practice of Pharmacy, 20th Edition.

Known excipients or carriers can also be added to optimize the specific use of the compositions, such as those described in the Handbook of Pharmaceutical Excipients, 6th Edition, Pharmaceutical Press, including film-forming agents, for example.

Examples of preferred formulations according to the present invention are gels, emulsions (oil in water (o/w) or water-in-oil (w/o)), creams, ointments, sprays, powders, lotions, mousses and mouthwashes.

The compositions more preferably take the form of an aqueous gel.

The aqueous gel can be prepared with a pharmaceutically acceptable polymer able to absorb a considerable quantity of water, and thus adhere to the mucous membranes (mucoadhesion).

The mucoadhesion of the compositions according to the invention ensures an adequate residence time on the mucous membranes, which are subject to the leaching action of physical and mechanical factors that can reduce the residence time of the active ingredient, for example in the case of the oral mucosa.

According to a further aspect of the invention, the compositions can also contain hyaluronic acid or pharmaceutically acceptable salts thereof, as a mucoadhesive polymer.

Hyaluronic acid or pharmaceutically acceptable salts thereof, with a molecular weight of between 800,000 and 4,000,000 Da, can preferably be used.

Even more preferably, the pharmaceutically acceptable salt of hyaluronic acid is the sodium salt.

Hyaluronic acid is extensively present in various tissues of the human and animal body; moreover, it is able to retain up to 1000 times its weight in water and has a high viscoelasticity level.

It has surprisingly been found that choline alfoscerate markedly improves the mucoadhesive property of the aqueous gel of hyaluronic acid, enhancing the mucoadhesion of hyaluronic acid, in particular hyaluronic acid sodium salt, and even more particularly with a molecular weight of between 800,000 and 4,000,000 Da, and vice versa.

This particular synergic action of the two compounds leads to greater therapeutic efficacy of both choline alfoscerate and hyaluronic acid.

In view of the results obtained with the compositions according to the invention, it can be assumed, by way of example but not of limitation, that the ingredients of the compositions according to the invention act through a reciprocal synergy mechanism; for example, due to its high level of hygroscopicity, choline alfoscerate can stabilize the composition containing hyaluronic acid, for example in gel form, and this allows hyaluronic acid to perform its mucoadhesive property as well as possible, and choline alfoscerate to be more therapeutically effective.

Moreover, in aqueous systems, an interaction may occur between the anionic function of hyaluronic acid and the cationic function of choline alfoscerate, which may help to further improve the mucoadhesion of hyaluronic acid and promote the residence of choline alfoscerate and hyaluronic acid on the mucous membranes.

The examples given below further illustrate the invention.

The percentages are expressed as parts by weight of the total volume of the composition.

EXAMPLE 1

Liquid Composition for the Oral Mucosa

| | |
|---|---|
| Choline alfoscerate | 10.00% |
| Preservative | q.s. |
| Flavouring | q.s. |
| Purified water | q.s. for 100% |

EXAMPLE 2

Mucoadhesive Liquid Composition for the Oral Mucosa

| | |
|---|---|
| Choline alfoscerate | 1.000% |
| Sodium hyaluronan (mean MW 1,500,000 Da) | 0.200% |
| Preservative | q.s. |
| Flavouring | q.s. |
| Purified water | q.s. for 100% |

EXAMPLE 3

Gel Composition for the Treatment of Mouth Ulcers

| | |
|---|---|
| Choline alfoscerate | 5.000% |
| Sodium alginate | 0.700% |
| Sorbitol | 7.000% |
| Preservative | q.s. |
| Flavouring | q.s. |
| Purified water | q.s. for 100% |

EXAMPLE 4

Mucoadhesive Gel Composition for the Treatment of Mouth Ulcers

| | |
|---|---|
| Choline alfoscerate | 0.500% |
| Sodium hyaluronan (mean MW 1,500,000 Da) | 0.100% |
| Sodium alginate | 0.600% |
| Sorbitol | 5.000% |
| Preservative | q.s. |
| Flavouring | q.s. |
| Purified water | q.s. for 100% |

EXAMPLE 5

Liquid Composition in Drop Form for Use on the Nasal Mucosa

| | |
|---|---|
| Choline alfoscerate | 0.100% |
| Camomile distilled water | 10.000% |
| Sodium chloride | 0.800% |
| Dibasic sodium phosphate dodecahydrate | 0.300% |
| Monobasic sodium phosphate monohydrate | 0.030% |
| Preservative | q.s. |
| Purified water | q.s. for 100% |

EXAMPLE 6

Liquid Composition in Mucoadhesive Gel Form for Use on the Nasal Mucosa

| | |
|---|---|
| Choline alfoscerate | 0.050% |
| Sodium hyaluronan (mean MW 1,500,000 Da) | 0.200% |
| *Euphrasia* distilled water | 10.000% |

-continued

| | |
|---|---|
| Sodium chloride | 0.800% |
| Dibasic sodium phosphate dodecahydrate | 0.300% |
| Monobasic sodium phosphate monohydrate | 0.030% |
| Preservative | q.s. |
| Purified water | q.s. for 100% |

EXAMPLE 7

Liquid Composition for Use on the Ocular Mucosa

| | |
|---|---|
| Choline alfoscerate | 0.010% |
| Witch hazel distilled water | 10.000% |
| Camomile distilled water | 10.000% |
| Sodium chloride | 0.800% |
| Dibasic sodium phosphate dodecahydrate | 0.300% |
| Monobasic sodium phosphate monohydrate | 0.030% |
| EDTA | 0.050% |
| Purified water | q.s. for 100% |

EXAMPLE 8

Mucoadhesive Liquid Composition for Use on the Ocular Mucosa

| | |
|---|---|
| Choline alfoscerate | 0.010% |
| Sodium hyaluronan (mean MW 1,500,000 Da) | 0.050% |
| Witch hazel distilled water | 10.000% |
| Camomile distilled water | 10.000% |
| Sodium chloride | 0.800% |
| Dibasic sodium phosphate dodecahydrate | 0.300% |
| Monobasic sodium phosphate monohydrate | 0.030% |
| EDTA | 0.050% |
| Purified water | q.s. for 100% |

EXAMPLE 9

Liquid Composition for Use on the Auricular Mucosa

| | |
|---|---|
| Choline alfoscerate | 0.100% |
| Glycerol | 50.000% |
| Purified water | q.s. for 100% |

EXAMPLE 10

Mucoadhesive Liquid Composition for Use on the Auricular Mucosa

| | |
|---|---|
| Choline alfoscerate | 0.100% |
| Sodium hyaluronan (mean MW 1,500,000 Da) | 0.100% |
| Glycerol | 50.000% |
| Purified water | q.s. for 100% |

EXAMPLE 11

Liquid Composition for Use on the Vaginal and Vulvar Mucosa

| | |
|---|---|
| Choline alfoscerate | 0.100% |
| Sodium chloride | 0.800% |
| Preservative | q.s. |
| Perfume | q.s. |
| Purified water | q.s. for 100% |

EXAMPLE 12

Mucoadhesive Liquid Composition for Use on the Vaginal and Vulvar Mucosa

| | |
|---|---|
| Choline alfoscerate | 0.050% |
| Sodium hyaluronan (mean MW 1,500,000 Da) | 0.200% |
| Sodium chloride | 0.800% |
| Preservative | q.s. |
| Perfume | q.s. |
| Purified water | q.s. for 100% |

EXAMPLE 13

Mucoadhesive Gel Composition for Use on the Vaginal and Vulvar Mucosa

| | |
|---|---|
| Choline alfoscerate | 0.025% |
| Sodium hyaluronan (mean MW 1,500,000 Da) | 0.150% |
| Carboxymethylcellulose sodium salt | 4.500% |
| Sodium chloride | 0.800% |
| Preservative | q.s. |
| Perfume | q.s. |
| Purified water | q.s. for 100% |

EXAMPLE 14

Mucoadhesive Gel Composition for Use on the Mucosa of the Male Genitals

| | |
|---|---|
| Choline alfoscerate | 0.500% |
| Sodium hyaluronan (mean MW 1,500,000 Da) | 0.250% |
| Carboxymethylcellulose sodium salt | 4.500% |
| Sodium chloride | 0.800% |
| Preservative | q.s. |
| Purified water | q.s. for 100% |

EXAMPLE 15

Mucoadhesive Gel Composition for Use on the Anorectal Mucosa

| | |
|---|---|
| Choline alfoscerate | 0.500% |
| Sodium hyaluronan (mean MW 1,500,000 Da) | 0.250% |
| Carboxymethylcellulose sodium salt | 4.500% |

EXAMPLE 16

Mucoadhesive Gel Composition for the Treatment of Inflamed Gums

| | |
|---|---|
| White thyme distilled water | 10.000% |
| Lavender distilled water | 10.000% |
| Cornflower distilled water | 10.000% |
| Sodium chloride | 0.800% |
| Preservative | q.s. |
| Purified water | q.s. for 100% |

EXAMPLE 16

Mucoadhesive Gel Composition for the Treatment of Inflamed Gums

| | |
|---|---|
| Choline alfoscerate | 1.000% |
| Sodium hyaluronan (mean MW 1,500,000 Da) | 0.200% |
| Xylitol | 3.500% |
| Carboxymethylcellulose sodium salt | 3.500% |
| Polyvinyl alcohol | 0.300% |
| Polycarbophil | 0.300% |
| Preservative | q.s. |
| Flavouring | q.s. |
| Colouring | q.s. |
| Purified water | q.s. for 100% |

EXAMPLE 17

Mucoadhesive Gel Composition for the Treatment of Damaged Gums

| | |
|---|---|
| Choline alfoscerate | 0.500% |
| Sodium hyaluronan (mean MW 1,500,000 Da) | 0.240% |
| Xylitol | 3.500% |
| Carboxymethylcellulose sodium salt | 3.700% |
| PEG 40 hydrogenated castor oil | 0.500% |
| Polyvinyl alcohol | 0.100% |
| Polycarbophil | 0.100% |
| Propylene glycol | 7.000% |
| Sodium benzoate | 1.000% |
| Preservative | q.s. |
| Flavouring | q.s. |
| Colouring | q.s. |
| Purified water | q.s. for 100 |

EXAMPLE 18

Mucoadhesive Composition in the Form of a Vaginal Pessary

| | |
|---|---|
| Choline alfoscerate | 0.100% |
| Sodium hyaluronan (mean MW 1,500,000 Da) | 0.200% |
| Gelatin | 20.000% |
| Glycerol | 70.000% |
| Purified water | q.s. for 100% |

EXAMPLE 19

Mucoadhesive Anorectal Enema Composition

| | |
|---|---|
| Choline alfoscerate | 0.300% |
| Sodium hyaluronan (mean MW 1,500,000 Da) | 0.300% |
| Colloidal silicon dioxide | 1.700% |
| Polyvinylpyrrolidone | 0.840% |
| Methylcellulose | 0.840% |
| Sodium benzoate | 0.400% |
| Potassium metabisulphite | 0.250% |
| Phosphoric acid | 0.100% |
| Purified water | q.s. for 100% |

EXAMPLE 20

Rectal Enema Composition (Ulcerating Colitis/Crohn's Disease)

| | |
|---|---|
| Choline alfoscerate | 0.050% |
| Mesalazine | 4.000% |
| Monobasic sodium phosphate monohydrate | 0.045% |
| Dibasic sodium phosphate dodecahydrate | 0.620% |
| Sodium chloride | 0.900% |
| Gum tragacanth | 0.400% |
| Preservative | q.s. |
| Purified water | q.s. for 100% |

The invention claimed is:

1. A method of treating inflamed mucous membranes comprising:
    administering an effective amount of a topical composition to said inflamed mucous membranes in need thereof, said composition consisting essentially of an amount of choline alfoscerate ranging between 0.010% w/v to 50% w/v and at least one pharmaceutically acceptable excipient or carrier, wherein the choline alfoscerate is the only active agent.

2. The method of claim 1, wherein said topical composition is administered to human or veterinary patients.

3. A method of treating inflammatory disorders of oral mucosa, said method comprising:
    topically administering an effective amount of a topical composition of claim 1 to an oral mucosa in need thereof.

4. The method of claim 3, wherein said oral mucosa comprises inflamed gums.

5. The method of claim 1, wherein said topical composition is administered
    by enema to the mucosa membrane of a patient suffering from ulcerative colitis or Crohn's disease.

6. The method of claim 5, wherein said mucosa membrane comprises anal and rectal mucosa.

* * * * *